US012662440B2

(12) United States Patent
Park et al.

(10) Patent No.: US 12,662,440 B2
(45) Date of Patent: *Jun. 23, 2026

(54) METHOD FOR PREPARING ISOPROPYL ALCOHOL

(71) Applicant: LG CHEM, LTD., Seoul (KR)

(72) Inventors: Sa Eun Park, Daejeon (KR); Sung Kyu Lee, Daejeon (KR); Tae Woo Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 875 days.

This patent is subject to a terminal disclaimer.

(21) Appl. No.: 17/791,858

(22) PCT Filed: Dec. 5, 2021

(86) PCT No.: PCT/KR2021/018303
§ 371 (c)(1),
(2) Date: Jul. 8, 2022

(87) PCT Pub. No.: WO2022/255575
PCT Pub. Date: Dec. 8, 2022

(65) Prior Publication Data
US 2024/0174586 A1     May 30, 2024

(30) Foreign Application Priority Data

May 31, 2021     (KR) ......................... 10-2021-0070248

(51) Int. Cl.
*C07C 29/17*     (2006.01)
*C07C 29/74*     (2006.01)

(52) U.S. Cl.
CPC ............ *C07C 29/172* (2013.01); *C07C 29/74* (2013.01)

(58) Field of Classification Search
CPC ....... C07C 29/172; C07C 29/74; C07C 29/76; C07C 29/78; C07C 29/04; C07C 29/17; C07C 31/10
USPC ...................................................... 568/840, 84
See application file for complete search history.

(56) References Cited

U.S. PATENT DOCUMENTS

| | | | |
|---|---|---|---|
| 2,834,816 A | 5/1958 | Levy et al. | |
| 4,469,903 A | 9/1984 | Schmidt | |
| 4,471,142 A | 9/1984 | Burton et al. | |
| 5,763,693 A * | 6/1998 | Hirata ..................... | C07C 29/04 |
| | | | 568/895 |
| 10,392,331 B2 | 8/2019 | Krupa | |
| 2008/0096985 A1 * | 4/2008 | Minta ................... | F25J 3/0271 |
| | | | 422/600 |

(Continued)

FOREIGN PATENT DOCUMENTS

| | | |
|---|---|---|
| CN | 1134410 A | 10/1996 |
| CN | 103664520 A | 3/2014 |

(Continued)

*Primary Examiner* — Fereydoun G Sajjadi
*Assistant Examiner* — Y. Lynnette Kelly-O'Neill
(74) *Attorney, Agent, or Firm* — Bryan Cave Leighton Paisner LLP

(57) ABSTRACT

A method of preparing isopropyl alcohol that allows separation of a reaction product stream formed by reacting a propylene monomer and water in a reactor into an unreacted propylene monomer and isopropyl alcohol with high purity using an absorption column, a gas purification column, and an inert gas removal column.

14 Claims, 2 Drawing Sheets

(56)          References Cited

U.S. PATENT DOCUMENTS

| | | | |
|---|---|---|---|
| 2010/0048960 A1* | 2/2010 | Degen .................. | C07C 29/095 |
| | | | 568/904 |
| 2010/0279181 A1* | 11/2010 | Adams, II ........... | H01M 8/0668 |
| | | | 429/410 |
| 2011/0190549 A1* | 8/2011 | Horton ................. | C07C 29/095 |
| | | | 568/885 |
| 2015/0025270 A1* | 1/2015 | Shimizu ................ | C07C 51/48 |
| | | | 203/7 |
| 2018/0201563 A1* | 7/2018 | Shimizu .............. | B01D 15/361 |

FOREIGN PATENT DOCUMENTS

| | | |
|---|---|---|
| CN | 103664520 B | 8/2015 |
| CN | 105272808 A | 1/2016 |
| CN | 105272806 B | 7/2017 |
| CN | 107501042 A | 12/2017 |
| CN | 105712839 B | 6/2019 |
| GB | 1337570 | 11/1973 |
| JP | 47031911 | 12/1972 |
| JP | H08291092 | 11/1996 |
| JP | 3693404 B2 | 9/2005 |
| JP | WO2017217279 A1 | 4/2019 |
| KR | 10-0219006 B1 | 9/1999 |
| KR | 10-1150101 B1 | 6/2012 |
| KR | 10-2019-0019060 A | 2/2019 |
| KR | 10-2020-0065579 A | 6/2020 |
| KR | 10-2021-0035735 A | 4/2021 |

* cited by examiner

【FIG. 1】
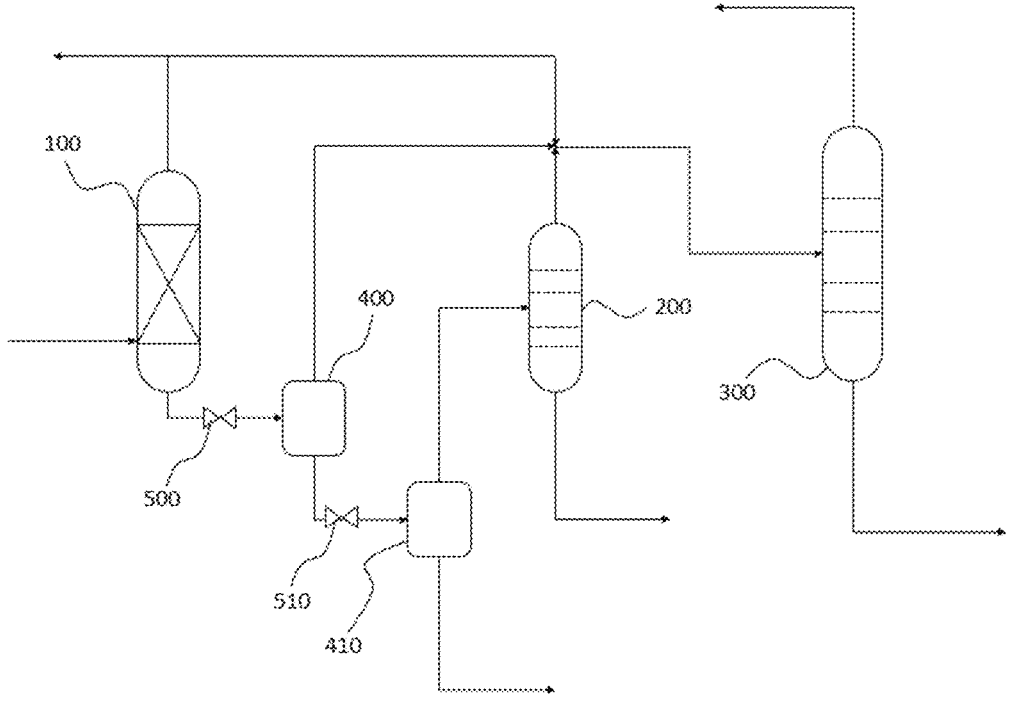
【FIG. 2】
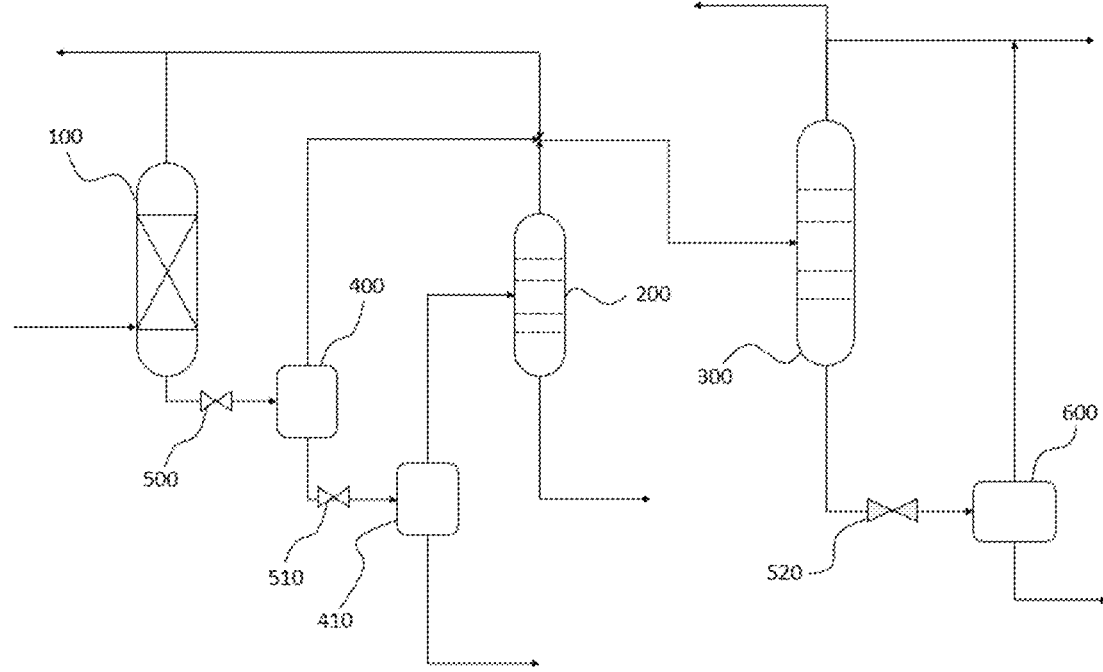

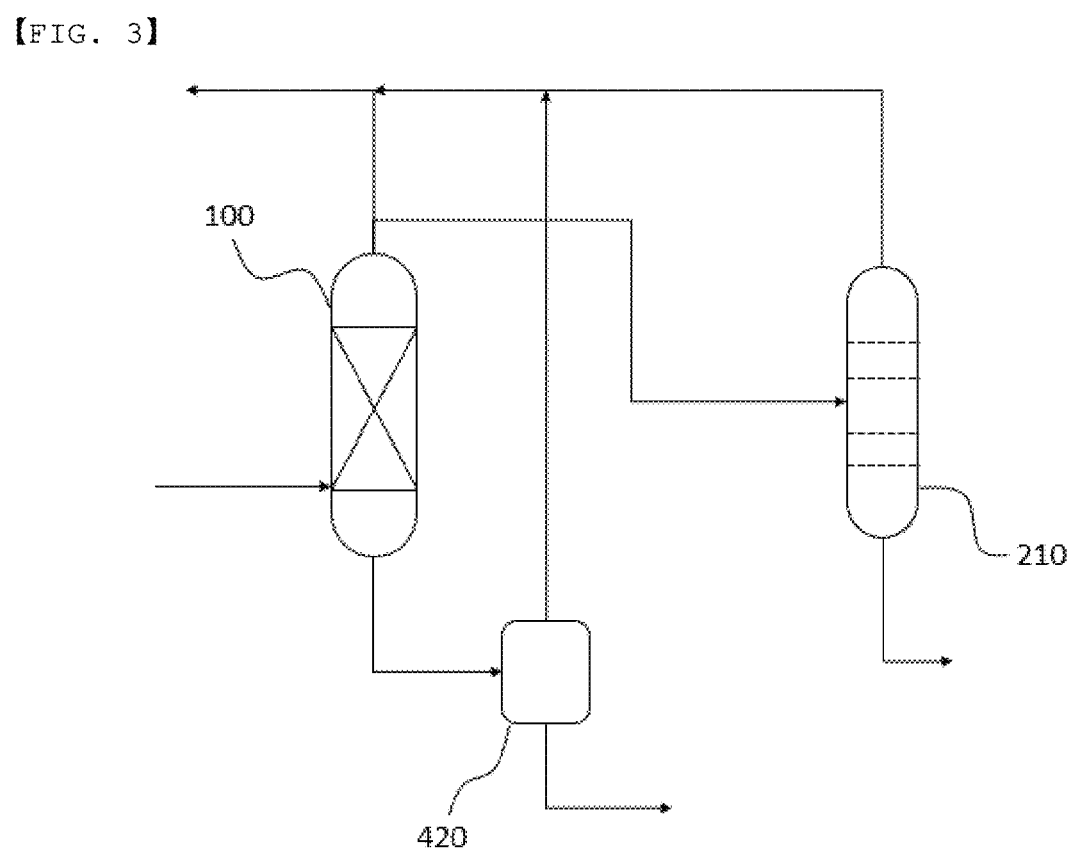

【FIG. 3】

METHOD FOR PREPARING ISOPROPYL ALCOHOL

CROSS-REFERENCE TO RELATED APPLICATIONS

This application is a US national phase of international application No. PCT/KR2021/018303, filed on Dec. 5, 2021, and claims the benefit of priority to Korean Patent Application No. 10-2021-0070248, filed on May 31, 2021, the entire contents of which are incorporated as if fully set forth herein.

TECHNICAL FIELD

The present invention relates to a method of preparing isopropyl alcohol, and more particularly, to a method of separating isopropyl alcohol with high purity from a reaction product of an isopropyl alcohol preparation process and effectively recovering an unreacted material.

BACKGROUND

Isopropyl alcohol (IPA) is used for various purposes including as a cleaning agent in the electronic industry such and in the manufacture of semiconductor or liquid crystal display (LCD).

In a process of preparing isopropyl alcohol, for example, propylene and water are used as raw material components. Here, the propylene and water are reacted to produce isopropyl alcohol.

The reaction product of the isopropyl alcohol preparation process includes isopropyl alcohol, an unreacted propylene monomer, and unreacted water. Isopropyl alcohol is separated from the reaction product of the isopropyl alcohol preparation process and recovered, and the unreacted propylene monomer is recovered and reused in the isopropyl alcohol preparation process.

Conventionally, various processes for separating isopropyl alcohol and an unreacted propylene monomer from the reaction product of the isopropyl alcohol preparation process and recovering and reusing the unreacted propylene monomer have been attempted. However, in the conventional isopropyl alcohol preparation process, the recovered unreacted propylene monomer includes isopropyl alcohol in a small amount, and thus, when the propylene monomer is supplied to a reactor and reused, a reverse reaction is caused in the reactor and a propylene conversion rate and selectivity of isopropyl alcohol are reduced. In addition, a propylene monomer is included in a stream supplied to an isopropyl alcohol purification section for purifying isopropyl alcohol to cause a loss of the propylene monomer.

In addition, the conventional isopropyl alcohol preparation process has a problem in that inert gas present in a propylene monomer supplied to a reactor is not removed and the inert gas accumulates in the process, and thus, a high-purity propylene monomer has to be used.

SUMMARY

To solve the problems mentioned above, an objective of the present invention is to provide a method of effectively recovering an unreacted material, and efficiently separating isopropyl alcohol and an unreacted propylene monomer from a reaction product of an isopropyl alcohol preparation process.

That is, an objective of the present invention, in separating a reaction product stream of a propylene monomer and water using an absorption column, a gas purification column, and an inert gas removal column, is to provide a method of preventing isopropyl alcohol from being included in a recovered stream, in recovering an unreacted propylene monomer in a reactor, and preventing unreacted propylene from being included in a stream supplied to an isopropyl alcohol purification section.

In one general aspect, a method of preparing isopropyl alcohol includes: supplying a reaction product stream formed by reacting a propylene monomer and water in a reactor to an absorption column; supplying a lower discharge stream including isopropyl alcohol from the absorption column to a gas purification column, supplying a part of an upper discharge stream including an unreacted propylene monomer from the absorption column to an inert gas removal column, and refluxing the rest of the upper discharge stream to the reactor; supplying an upper discharge stream including the unreacted propylene monomer from the gas purification column to the inert gas removal column and supplying a lower discharge stream including isopropyl alcohol from the gas purification column to an isopropyl alcohol purification section; and refluxing an upper discharge stream including the unreacted propylene monomer from the inert gas removal column to the reactor and supplying a lower discharge stream including isopropyl alcohol from the inert gas removal column to an isopropyl alcohol purification section.

According to the method of preparing isopropyl alcohol of the present invention, separation efficiency may be increased when separating a reaction product in an isopropyl alcohol preparation process by a reaction of a propylene monomer and water, using an absorption column, a gas purification column, and an inert gas removal column.

In addition, by increasing the separation efficiency, inclusion of isopropyl alcohol in an unreacted propylene monomer circulating to a reactor is prevented to promote a forward reaction of an equilibrium reaction in the reactor to increase isopropyl alcohol production, and an outflow of the unreacted propylene monomer into a stream supplied to an isopropyl alcohol purification section is prevented to reduce a loss of the propylene monomer.

In addition, the inert gas removal column is used to remove inert gas, thereby preventing accumulation of the inert gas in the process.

In addition, the supply stages of a stream supplied to the inert gas removal column are controlled, thereby improving separation efficiency.

In addition, the lower discharge stream from the absorption column is pre-separated using one or more flash drums before supplying the lower discharge stream to the gas purification column, thereby improving the separation efficiency of the gas purification column and reducing a device size of a rear end column.

BRIEF DESCRIPTION OF DRAWINGS

FIGS. 1 and 2 are process flow diagrams of a method of preparing isopropyl alcohol according to exemplary embodiments of the present invention.

FIG. 3 is a process flow diagram of a method of preparing isopropyl alcohol according to a comparative example.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention may refer to a fluid flow in a process, or may refer to a fluid itself flowing in a pipe. Specifically, the stream may refer to both a fluid flowing in a pipe connecting each device and a fluid flow. In addition, the fluid may refer to a gas or a liquid. Herein, a case in which a solid component is included in the fluid is not excluded.

Hereinafter, the present invention will be described in more detail referring to FIGS. 1 and 2, for better understanding of the present invention.

According to the present invention, a method of preparing isopropyl alcohol is provided. The isopropyl alcohol may be produced by a process of reacting a propylene monomer and water in a vapor phase. Specifically, a feed stream including a propylene monomer and water is supplied to a reactor and a reaction product produced in the reactor may include isopropyl alcohol, an unreacted propylene monomer, and unreacted water. Here, isopropyl alcohol is separated from the reaction product and recovered, and the unreacted propylene monomer is recovered and reused in the isopropyl alcohol preparation process.

Conventionally, various processes for separating isopropyl alcohol and an unreacted propylene monomer from the reaction product of the isopropyl alcohol preparation process and recovering and reusing the unreacted propylene monomer have been attempted. However, in the conventional isopropyl alcohol preparation process, the recovered unreacted propylene monomer includes isopropyl alcohol in a small amount, and thus, when the propylene monomer is supplied to a reactor and reused, a reverse reaction is caused in the reactor and a propylene conversion rate and selectivity of isopropyl alcohol are reduced and the production of isopropyl alcohol is decreased. In addition, a propylene monomer is included in a stream supplied to an isopropyl alcohol purification section for purifying isopropyl alcohol, which causes a loss of the propylene monomer.

To solve the conventional problems described above, a method is provided herewith, in which, when an unreacted propylene monomer is recovered from a reaction product of an isopropyl alcohol preparation process and reused in a reactor, separation efficiency of isopropyl alcohol and a propylene monomer is maximized to prevent isopropyl alcohol from being included in the unreacted propylene monomer to be recovered, thereby promoting a forward reaction of an equilibrium reaction in the reactor to increase a production of isopropyl alcohol, and preventing an outflow of the unreacted propylene monomer in a stream supplied to an isopropyl alcohol purification section to reduce a loss of the propylene monomer.

According to an exemplary embodiment of the present invention, a method of preparing isopropyl alcohol includes: supplying a reaction product stream formed by reacting a propylene monomer and water in a reactor to an absorption column 100; supplying a lower discharge stream including isopropyl alcohol from the absorption column 100 to a gas purification column 200, supplying a part of an upper discharge stream including an unreacted propylene monomer from the absorption column 100 to an inert gas removal column 300, and refluxing the rest of the upper discharge stream to the reactor; supplying an upper discharge stream including the unreacted propylene monomer from the gas purification column 200 to the inert gas removal column 300 and supplying a lower discharge stream including isopropyl alcohol from the gas purification column 200 to an isopropyl alcohol purification section; and refluxing an upper discharge stream including the unreacted propylene monomer from the inert gas removal column 300 to the reactor and supplying a lower discharge stream including isopropyl alcohol from the inert gas removal column to an isopropyl alcohol purification section.

According to an exemplary embodiment of the present invention, a feed stream including a propylene monomer and water may be supplied to the reactor and a gaseous reaction may be performed to prepare a reaction product including isopropyl alcohol. A mole ratio of water to the propylene monomer included in the feed stream may be 0.3 to 0.5, 0.35 to 0.5, or 0.35 to 0.45. By satisfying the mole ratio of water to the propylene monomer in the feed stream supplied to the reactor, a forward reaction of an equilibrium reaction is promoted and the progress of a reverse reaction may be prevented to increase the production of isopropyl alcohol.

According to an exemplary embodiment of the present invention, the reactor may be operated under optimal conditions to efficiently prepare isopropyl alcohol by a gaseous reaction of a propylene monomer and water. For example, the operating pressure of the reactor may be 30 $kg/cm^2 \cdot g$ to 50 $kg/cm^2 \cdot g$, 35 $kg/cm^2 \cdot g$ to 50 $kg/cm^2 \cdot g$, or 35 $kg/cm^2 \cdot g$ to 45 $kg/cm^2 \cdot g$, and the operating temperature may be 180° C. to 220° C., 185° C. to 220° C., or 190° C. to 215° C. By operating the reactor in these pressure and temperature ranges, isopropyl alcohol may be effectively produced by a gaseous reaction using the propylene monomer and water.

According to an exemplary embodiment of the present invention, the reaction product produced by the gaseous reaction of the propylene monomer and water in the reactor is gaseous, and may include isopropyl alcohol, an unreacted propylene monomer, and unreacted water. The gaseous reaction product discharged from the reactor may be condensed into a liquid reaction product using one or more heat exchangers and then supplied to an absorption column 100. Here, the temperature of the reaction product supplied to the absorption column 100 is, for example, 105° C. to 150° C., 110° C. to 140° C., or 115° C. to 140° C.

According to an exemplary embodiment of the present invention, the gaseous reaction product discharged from the reactor may be heat-exchanged with a feed stream supplied from one or more heat exchangers to the reactor. The feed stream passing through the one or more heat exchangers may be heated to the temperature of, for example, 170° C. to 210° C., 180° C. to 200° C., or 185° C. to 195° C.

As such, by heat-exchanging the gaseous reaction product stream discharged from the reactor with the feed stream supplied to the reactor, the gaseous reaction product discharged from the reactor may be condensed into a liquid reaction product and the feed stream may be supplied to the reactor after being pre-heated. Thus, energy for heating to an optimal temperature for efficiently preparing isopropyl alcohol before supplying the feed stream to the reactor may be reduced, and coolant costs required for condensation to a temperature for increasing separation efficiency by supplying the gaseous reaction product to the absorption column 100 may be reduced.

According to an exemplary embodiment of the present invention, the gaseous reaction product passes through one or more heat exchangers to be partly condensed to a liquid reaction product and the rest thereof may be present as the gaseous reaction product. As an example, the gaseous reaction product discharged from the reactor may pass through one or more heat exchangers to be separated into a gaseous first reaction product stream and a liquid second reaction product stream. Here, the first reaction product stream and the second reaction product stream may be separated and discharged through a separate pipe formed in a rear end heat exchanger, or separated through a gas-liquid separation device installed at a rear end of the heat exchanger.

According to an exemplary embodiment of the present invention, a ratio of the flow rate of the first reaction product stream to the flow rate of the second reaction product stream may be 5 to 11, 6 to 10, or 7 to 9. As described above, in a process of heat-exchanging the gaseous reaction product stream discharged from the reactor with the feed stream in one or more heat exchangers, the gaseous reaction product stream discharged from the reactor is cooled to a temperature of 105° C. to 150° C., thereby controlling the ratio of the flow rate of the first reaction product stream to the flow rate of the second reaction product stream to 5 to 11. Herein, the "flow rate" may be measured in units of weight per unit hour. As a specific example, the unit of the flow rate may be ton/hr.

According to an exemplary embodiment of the present invention, the first reaction product stream may be further condensed using a cooler and supplied to the absorption column 100 as a gas-liquid mixed phase in which a gas phase and a liquid phase are mixed. Here, the first reaction product stream passes through one or more heat exchangers and is in a state of being cooled as described above, and the coolant used in the cooler may be replaced with low-priced cooling water and the usage of the cooling water may be minimized.

According to an exemplary embodiment of the present invention, the gaseous first reaction product stream may include 85 wt % to 95 wt % of the unreacted propylene monomer, 4 wt % to 8 wt % of isopropyl alcohol, and 1 wt % to 5 wt % of water. Specifically, it is recognized that the first reaction product stream includes a high content of the unreacted propylene monomer and a low content of isopropyl alcohol and water.

In addition, the liquid second reaction product stream may include 1 wt % to 10 wt % of the unreacted propylene monomer, 5 wt % to 15 wt % of isopropyl alcohol, and 80 wt % to 90 wt % of water. Specifically, the second reaction product stream may have a low content of the unreacted propylene monomer and a high content of water. Here, the content of isopropyl alcohol included in the second reaction product stream may be higher than the content of isopropyl alcohol included in the first reaction product stream.

According to an exemplary embodiment of the present invention, the first reaction product stream and the second reaction product stream in a gas-liquid mixed phase may be supplied to a lower side of the absorption column 100 as individual streams or a mixed stream.

According to an exemplary embodiment of the present invention, the total number of stages of the absorption column 100 may be 10 to 30, 15 to 30, or 15 to 25. For example, when the total number of stages of the absorption column 100 is 10, the first reaction product and the second reaction product may be supplied to the 10th stage of the absorption column 100.

According to an exemplary embodiment of the present invention, the reaction product is supplied to the absorption column 100, and a lower discharge stream including isopropyl alcohol and an upper discharge stream including the unreacted propylene monomer may be separated in the absorption column 100. Here, the upper discharge stream from the absorption column 100 may further include inert gas together with the unreacted propylene monomer, and the lower discharge stream may further include unreacted water together with isopropyl alcohol. Specifically, the reaction product may be supplied to a lower end of the absorption column 100, isopropyl alcohol included in the reaction product is dissolved using a solvent supplied to the absorption column 100 to be separated into a lower portion of the absorption column 100, and the stream including the unreacted propylene monomer may be separated into an upper portion.

The solvent used in the absorption column 100 may be, for example, water. By using, which is a component used in the reaction as the solvent, a separate device for separating the solvent in the rear end is not required.

The flow rate of the solvent supplied to the absorption column 100 may be 20% to 50%, 20% to 45%, or 25% to 40% of the total flow rate of the reaction product supplied to the absorption column 100. The solvent is supplied at the flow rate within these ranges to improve the absorbency of isopropyl alcohol included in the reaction product supplied to the absorption column 100 while preventing an excessive increase of energy costs for recovering the solvent at the rear end.

According to an exemplary embodiment of the present invention, the operating pressure of the absorption column 100 may be 20 kg/cm²·g to 40 kg/cm²·g, 25 kg/cm²·g to 40 kg/cm²·g, or 25 kg/cm²·g to 35 kg/cm²·g, and the operating temperature thereof may be 80° C. to 110° C., 90° C. to 110° C., or 90° C. to 100° C. By operating the absorption column 100 at the pressure and the temperature in the above ranges, the upper discharge stream including the unreacted propylene monomer and the lower discharge stream including isopropyl alcohol may be effectively separated.

According to an exemplary embodiment of the present invention, the lower discharge stream from the absorption column 100 may include a small amount of the unreacted propylene monomer in addition to isopropyl alcohol and unreacted water. For example, the content of the unreacted propylene monomer included in the lower discharge stream from the absorption column 100 may be 5 wt % or less or 3 wt % to 5 wt %. Thus, all or a part of the lower discharge stream including isopropyl alcohol from the absorption column 100 is supplied to a gas purification column 200 to separate the unreacted propylene monomer included in the lower discharge stream from the absorption column 100 as an upper discharge stream, and a lower discharge stream including isopropyl alcohol and unreacted water may be supplied to an isopropyl alcohol purification section.

According to an exemplary embodiment of the present invention, the lower discharge stream from the absorption column 100 may pass through one or more, one to three, or one or two flash drums before being supplied to the gas purification column 200. For example, a part of the lower discharge stream from the absorption column 100 may be supplied to the gas purification column 200 using a first flash drum 400 or the first flash drum 400 and a second flash drum 410.

As an example, when one flash drum is used, the lower discharge stream from the absorption column may be supplied to the first flash drum, the unreacted propylene monomer included in the lower discharge stream from the absorption column may be separated as an upper discharge stream and supplied to the gas purification column, and a lower discharge stream may be supplied to the isopropyl alcohol purification section.

Before the lower discharge stream from the absorption column is supplied to the first flash drum, the stream may be depressurized using a first valve and then supplied to the flash drum, thereby improving the separation efficiency of a gas phase and a liquid phase in the first flash drum.

The lower discharge stream from the absorption column is pre-separated through the first flash drum, and a part of the stream including the unreacted propylene monomer and inert gas is supplied to the gas purification column and another part of the stream including isopropyl alcohol and unreacted water may be supplied to the isopropyl alcohol purification section.

In addition, the outflow of isopropyl alcohol into an upper discharge stream from the inert gas removal column may be prevented by controlling the composition of the stream supplied to an inert gas removal column to improve separation efficiency. For example, isopropyl alcohol in the stream supplied to the inert gas removal column is all separated into a lower portion of the inert gas removal column, and the unreacted propylene monomer which does not include isopropyl alcohol may be recovered with high purity, and refluxed to the reactor and reused.

As another example, the lower discharge stream from the absorption column 100 may be supplied to the first flash drum 400, the unreacted propylene monomer included in the lower discharge stream from the absorption column 100 may be separated as the upper discharge stream and supplied to an inert gas removal column 300, and the lower discharge stream may be supplied to the second flash drum 410.

Before supplying the lower discharge stream from the absorption column 100 to the first flash drum 400, the stream may be depressurized using a first valve 500 and then supplied to the first flash drum 400. In addition, before the lower discharge stream from the first flash drum 400 is supplied to the second flash drum 410, the stream may be depressurized using a second valve 510 and then supplied to the second flash drum 410. Thus, separation efficiency of a gas phase and a liquid phase in each of the first flash drum 400 and the second flash drum 410 may be improved.

The lower discharge stream including isopropyl alcohol and unreacted water from the second flash drum 410 may be supplied to the isopropyl alcohol purification section, and the upper discharge stream including the remaining components may be supplied to the gas purification column 200.

The lower discharge stream from the absorption column 100 may be pre-separated using the first flash drum 400 and the second flash drum 410, a part of the stream including the unreacted propylene monomer and inert gas may be supplied to the inert gas removal column 300, and another part of the stream including isopropyl alcohol and unreacted water may be supplied to the isopropyl alcohol purification section.

In addition, the outflow of isopropyl alcohol into an upper discharge stream from the inert gas removal column 300 may be prevented by controlling the composition of the stream supplied to the inert gas removal column 300 to improve separation efficiency. For example, isopropyl alcohol in the stream supplied to the inert gas removal column 300 is all separated into the lower portion of the inert gas removal column 300, and the unreacted propylene monomer which does not include isopropyl alcohol may be recovered with high purity, and refluxed to the reactor and reused.

As such, the lower discharge stream from the absorption column 100 is depressurized and a space for separating a gas phase and a liquid phase before supplying the stream to a rear end column is provided when the lower discharge stream from the absorption column 100 is pre-separated using one or more flash drums, thereby preventing an inefficient increase in a size of the column for gas-liquid separation in the rear end column, and improving the separation efficiency of the gas purification column 200 and the inert gas removal column 300.

According to an exemplary embodiment of the present invention, a flow rate ratio between the upper discharge stream from the first flash drum 400 and the upper discharge stream from the second flash drum 410 may be 1:0.4 to 1:0.8, 1:0.5 to 1:0.8, or 1:0.5 to 1:0.7. By controlling the flow rate ratio of the upper discharge stream from the first flash drum 400 and the upper discharge stream from the second flash drum 410 to be within the above ranges, a pre-separation effect is improved and also the components and the flow rate of the stream supplied to the gas purification column 200 and the inert gas removal column 300 may be controlled to reduce the device size of the column and improve separation efficiency rate.

According to an exemplary embodiment of the present invention, the operating temperature in the first flash drum 400 may be 80° C. to 100° C., 85° C. to 100° C., or 85° C. to 95° C. In addition, the operating pressure in the first flash drum 400 may be 10 kg/cm²·g to 25 kg/cm²·g, 15 kg/cm²·g to 25 kg/cm²·g, or 15 kg/cm²·g to 20 kg/cm²·g. When the operating conditions in the first flash drum 400 are controlled to be in these ranges, the separation efficiency may be improved.

The operating temperature in the second flash drum 410 may be 80° C. to 95° C., 85° C. to 95° C., or 85° C. to 90° C. In addition, the operating pressure in the second flash drum 410 may be 0 kg/cm²·g to 2 kg/cm²·g, 0 kg/cm²·g to 1 kg/cm²·g, or 0 kg/cm²·g to 0.5 kg/cm²·g. When the operating conditions in the second flash drum 410 are controlled to be in these ranges, the separation efficiency may be improved.

According to an exemplary embodiment of the present invention, the upper discharge stream including the unreacted propylene monomer and the lower discharge stream including isopropyl alcohol may be separated in the gas purification column 200. Here, the upper discharge stream from the gas purification column 200 may further include inert gas together with the unreacted propylene monomer, and the lower discharge stream may further include unreacted water together with isopropyl alcohol. Specifically, the upper discharge stream including the unreacted propylene monomer in the gas purification column 200 may be supplied to the inert gas removal column 300 and the lower discharge stream including isopropyl alcohol may be supplied to the isopropyl alcohol purification section.

The operating pressure of the gas purification column 200 may be 0 kg/cm²·g to 2 kg/cm²·g, 0 kg/cm²·g to 1 kg/cm²·g, or 0 kg/cm²·g to 0.5 kg/cm²·g, and the operating temperature may be 40° C. to 80° C., 50° C. to 80° C., or 50° C. to 70° C. By operating the gas purification column 200 in the above operating temperature and pressure ranges, the propylene monomer may be separated with high purity into the upper discharge stream.

According to an exemplary embodiment of the present invention, the stream supplied to the inert gas removal column 300 may form a mixed stream and be supplied to the inert gas removal column 300. For example, a part of the upper discharge stream from the absorption column 100 and the upper discharge stream from the gas purification column 200 may form a mixed stream and be supplied to the inert gas removal column 300, and if necessary, a part of the upper discharge stream from the absorption column 100, the upper discharge stream from the gas purification column 200, and the upper discharge stream from the first flash drum 400 may form a mixed stream and be supplied to the inert gas removal column 300.

According to an exemplary embodiment of the present invention, a ratio of the total number of stages of the gas purification column 200 to the inert gas removal column 300 may be 1:15 to 1:20, 1:17 to 1:20, or 1:17 to 1:18. Here, the total number of stages of the gas purification column 200 may be 3 to 15, 3 to 10, or 3 to 5, and the total number of stages of the inert gas removal column 300 may be 50 to 90, 65 to 90, or 65 to 75. As described above, by controlling the total number of stages and the ratio of the total number of stages of the gas purification column 200 to the inert gas removal column 300, the composition of the upper discharge stream from the gas purification column 200 may be controlled and the separation efficiency in the inert gas removal column 300 may be improved.

According to an exemplary embodiment of the present invention, the mixed stream may be supplied to a stage at 5% to 25%, 10% to 25%, or 10% to 20% of the total number of stages of the inert gas removal column 300. Specifically, when the mixed stream is supplied to the stage of the inert gas removal column 300 at the above ranges, a stripping section in which inert gas and unreacted propylene are separated into an upper portion is sufficiently secured, thereby improving the separation efficiency.

According to an exemplary embodiment of the present invention, the inert gas removal column 300 may be supplied with the upper discharge stream from the absorption column 100, the upper discharge stream from the gas purification column 200, and the upper discharge stream from the first flash drum 400, and may separate the unreacted propylene monomer as an upper discharge stream and separate isopropyl alcohol and unreacted water as a lower discharge stream. Specifically, inert gas may be separated as a gaseous upper discharge stream and the unreacted propylene monomer may be separated as a liquid upper discharge stream of the inert gas removal column 300. Here, the liquid upper discharge stream from the inert gas removal column 300 may be refluxed to the reactor and the lower discharge stream from the inert gas removal column may be supplied to the isopropyl alcohol purification section.

According to an exemplary embodiment of the present invention, the operating pressure of the inert gas removal column 300 may be 15 kg/cm²·g to 25 kg/cm²·g, 18 kg/cm²·g to 25 kg/cm²·g, or 18 kg/cm²·g to 20 kg/cm²·g, and the operating temperature thereof may be 40° C. to 170° C., 45° C. to 170° C., or 45° C. to 160° C. By operating the inert gas removal column 300 at the pressure and temperature ranges above, each component may be separated with high purity through an upper portion and a lower portion.

According to an exemplary embodiment of the present invention, by separating and removing the inert gas, for example, ethane, as the upper discharge stream from the inert gas removal column 300, accumulation of the inert gas in the process may be prevented. Specifically, in the isopropyl alcohol preparation process performed in a gaseous reaction, a part of inert gas may be included in the propylene monomer introduced as a reactant. The inert gas may include, for example, one or more selected from the group consisting of hydrocarbons having 2 or 3 carbon atoms, and as a specific example, the inert gas may include one or more selected from the group consisting of ethane and propane. Here, the gaseous component including the inert gas in the upper discharge stream from the inert gas removal column 300 is purged to separate and remove a part or all of the amount of the inert gas, thereby lowering the content of the inert gas in the liquid component of the upper discharge stream from the inert gas removal column 300 refluxed to the reactor so that the inert gas is not accumulated in the process.

According to an exemplary embodiment of the present invention, the lower discharge stream from the inert gas removal column 300 is a stream including isopropyl alcohol and unreacted water, and may pass through a third valve 520 and be supplied to a gas-liquid separation device 600 after depressurization. The lower discharge stream including isopropyl alcohol and water from the gas-liquid separation device 600 is supplied to the isopropyl alcohol purification section, and the upper discharge stream including the inert gas, for example, propane, may be removed by purging with a gaseous component in the upper discharge stream from the inert gas removal column 300. In this case, the inert gas in the stream supplied to the isopropyl alcohol purification section is removed so that the inert gas is not accumulated in the process.

According to an exemplary embodiment of the present invention, the stream supplied to the isopropyl alcohol purification section may include isopropyl alcohol, unreacted water, and water used as a solvent, and high-purity isopropyl alcohol from which water is removed in the isopropyl alcohol purification section may be separated. Here, water separated in the isopropyl alcohol purification section may be supplied to the reactor and reused, and in this case, impurities such as a propylene monomer or isopropyl alcohol are not included, so that it may be easy to control a mole ratio of water to the propylene monomer in preparing isopropyl alcohol in the reactor.

According to an exemplary embodiment of the present invention, devices such as a distillation column, a condenser, a reboiler, a valve, a pump, a separator, and a mixer may be further installed and used in the method of preparing isopropyl alcohol, if necessary.

Hereinabove, the method of preparing isopropyl alcohol according to the present invention has been described and illustrated in the drawings, but the description and the illustration in the drawings are of only core components for understanding of the present invention, and in addition to the process and apparatus described above and illustrated in the drawings, the process and the apparatus which are not described and illustrated separately may be appropriately applied and used for carrying out the method of preparing isopropyl alcohol according to the present invention.

Hereinafter, the present invention will be described in more detail by the Examples. However, the following Examples are provided for illustrating the present invention, and it is apparent to a person skilled in the art that various modifications and alterations may be made without departing from the scope and spirit of the present invention and the scope of the present invention is not limited thereto.

EXAMPLES

Example 1

As shown in the process flow diagram of FIG. 1, a reaction product including isopropyl alcohol (IPA) was prepared, and a process of separating isopropyl alcohol from the reaction product was simulated using Aspen Plus available from Aspen Technology Inc.

Specifically, a feed stream was supplied at a flow rate of 10 ton/hr to a reactor operating at a pressure of 40 kg/cm²·g and a temperature of 192° C. to 208° C., a mole ratio of water ($H_2O$) to a propylene monomer (PP) in the feed stream was controlled to 0.4, and inert gas included ethane and propane.

A gaseous reaction product stream discharged from the reactor passed through two heat exchangers and was separated into and discharged as a gaseous first reaction product stream and a liquid second reaction product stream, and the first reaction product stream was partly condensed into a liquid phase in a cooler and then supplied to the 20th stage of an absorption column 100, and the second reaction product stream was supplied to the 20th stage of the absorption column 100. At this time, the total number of stages of the absorption column 100 was 20.

The absorption column 100 was operated at a temperature of 96° C. to 98° C. and a pressure of 31.2 kg/cm²·g to 31.6 kg/cm²·g, isopropyl alcohol in the reaction product stream was absorbed using water supplied as a solvent in the upper end of the absorption column 100, and separated into an upper discharge stream including a propylene monomer and a lower discharge stream including water and isopropyl alcohol. Specifically, a part of the upper discharge stream from the absorption column 100 was supplied to an inert gas removal column 300, the rest of the stream was refluxed to the reactor, and the lower discharge stream was depressurized using a first valve 500 and then supplied to a first flash drum 400. The first flash drum 400 was operated at an operating pressure of 16.8 kg/cm²·g and the flow rate of the upper discharge stream was controlled to 0.2 ton/hr.

The lower discharge stream in the first flash drum 400 was depressurized using a second valve 510 and then supplied to the second flash drum 410, and the upper discharge stream from the second flash drum 410 was supplied to a gas purification column 200 and the lower discharge stream from the second flash drum was supplied to an isopropyl alcohol purification section. The second flash drum 410 was operated at an operating pressure of 0.2 kg/cm²·g and the flow rate of the upper discharge stream was controlled to 0.1 ton/hr.

The lower discharge stream from the gas purification column 200 was supplied to the isopropyl alcohol purification section. The total number of stages of the gas purification column 200 was 4, and the operating temperature was controlled to 57° C. to 64° C. and the operating pressure was controlled to 0.15 kg/cm²·g to 0.2 kg/cm²·g.

A part of the upper discharge stream from the absorption column 100, the upper discharge stream from the gas purification column 200, and the upper discharge stream from the first flash drum 400 formed a mixed stream and was supplied to the 9th stage of the inert gas removal column 300. At this time, the total number of stages of the inert gas removal column 300 was 70, and the operating temperature was controlled to 46° C. to 157° C. and the operating pressure was controlled to 19.1 kg/cm²·g to 19.6 kg/cm²·g.

In the inert gas removal column 300, the unreacted propylene monomer in the upper discharge stream was refluxed to the reactor and reused, and the lower discharge stream was supplied to the isopropyl alcohol purification section to obtain isopropyl alcohol from which water was removed.

(1) The content of isopropyl alcohol in the upper discharge stream from the inert gas removal column 300 refluxed to the reactor, (2) the content of the propylene monomer in the upper discharge stream from the inert gas removal column 300 refluxed to the reactor, and (3) the content of the propylene monomer in the stream supplied to the isopropyl alcohol purification section are shown in Table 1.

Example 2

As shown in the process flow diagram of FIG. 2, a reaction product including isopropyl alcohol (IPA) was prepared, and a process of separating isopropyl alcohol from the reaction product was simulated using Aspen Plus available from Aspen Technology Inc.

Specifically, a feed stream was supplied at a flow rate of 10 ton/hr to a reactor operating at a pressure of 40 kg/cm²·g and a temperature of 192° C. to 208° C., a mole ratio of water ($H_2O$) to a propylene monomer (PP) in the feed stream was controlled to 0.4, and inert gas included ethane and propane.

A gaseous reaction product stream discharged from the reactor passed through two heat exchangers and was separated into and discharged as a gaseous first reaction product stream and a liquid second reaction product stream, and the first reaction product stream was partly condensed into a liquid phase in a cooler and then supplied to the 20th stage of an absorption column 100, and the second reaction product stream was supplied to the 20th stage of the absorption column 100. The total number of stages of the absorption column 100 was 20.

The absorption column 100 was operated at a temperature of 96° C. to 98° C. and a pressure of 31.2 kg/cm²·g to 31.6 kg/cm²·g, isopropyl alcohol in the reaction product stream was absorbed using water supplied as a solvent in the upper end of the absorption column 100, and was separated into an upper discharge stream including a propylene monomer and a lower discharge stream including water and isopropyl alcohol. Specifically, a part of the upper discharge stream from the absorption column 100 was supplied to an inert gas removal column 300, the rest of the stream was refluxed to the reactor, and the lower discharge stream was depressurized using a first valve 500 and then supplied to a first flash drum 400. The first flash drum 400 was operated at an operating pressure of 16.8 kg/cm²·g and the flow rate of the upper discharge stream was controlled to 0.2 ton/hr.

The lower discharge stream in the first flash drum 400 was depressurized using a second valve 510 and then supplied to the second flash drum 410 and the upper discharge stream from the second flash drum 410 was supplied to a gas purification column 200 and the lower discharge stream from the second flash drum was supplied to an isopropyl alcohol purification section. The second flash drum 410 was operated at an operating pressure of 0.2 kg/cm²·g and the flow rate of the upper discharge stream was controlled to 0.1 ton/hr.

The lower discharge stream from the gas purification column 200 was supplied to the isopropyl alcohol purification section. The total number of stages of the gas purification column 200 was 4, and the operating temperature was controlled to 57° C. to 64° C. and the operating pressure was controlled to 0.15 kg/cm²·g to 0.2 kg/cm²·g.

A part of the upper discharge stream from the absorption column 100, the upper discharge stream from the gas purification column 200, and the upper discharge stream from the first flash drum 400 formed a mixed stream and was supplied to the 9th stage of the inert gas removal column 300.

The gaseous component including ethane in the upper discharge stream from the inert gas removal column 300 was discharged to be removed, the liquid component including the unreacted propylene monomer was refluxed to the reactor and reused, and the lower discharge stream was depressurized using a third valve 520 and then supplied to a gas-liquid separation device 600. In the gas-liquid separation device 600, propane was separated as the upper discharge stream and discharged with the gaseous component in the upper discharge stream from the inert gas removal column 300, and the lower discharge stream was supplied to the isopropyl alcohol purification section to obtain isopropyl alcohol from which water was removed. The total number of stages of the inert gas removal column 300 was 70, and the operating temperature was controlled to 46° C. to 157° C. and the operating pressure was controlled to 19.1 kg/cm²·g to 19.6 kg/cm²·g.

(1) The content of isopropyl alcohol in the upper discharge stream from the inert gas removal column 300 refluxed to the reactor, (2) the content of the propylene monomer in the upper discharge stream from the inert gas removal column 300 refluxed to the reactor, and (3) the content of the propylene monomer in the stream supplied to the isopropyl alcohol purification section are shown in Table 1.

Example 3

Isopropyl alcohol was prepared in the same manner as in Example 2, except that the mixed stream was supplied to the third stage of the inert gas removal column 300.

(1) The content of isopropyl alcohol in the upper discharge stream from the inert gas removal column 300 refluxed to the reactor, (2) the content of the propylene monomer in the upper discharge stream from the inert gas removal column 300 refluxed to the reactor, and (3) the content of the propylene monomer in the stream supplied to the isopropyl alcohol purification section are shown in Table 1.

Example 4

Isopropyl alcohol was prepared in the same manner as in Example 2, except that the mixed stream was supplied to the 19th stage of the inert gas removal column 300.

(1) The content of isopropyl alcohol in the upper discharge stream from the inert gas removal column 300 refluxed to the reactor, (2) the content of the propylene monomer in the upper discharge stream from the inert gas removal column 300 refluxed to the reactor, and (3) the content of the propylene monomer in the stream supplied to the isopropyl alcohol purification section are shown in Table 1.

COMPARATIVE EXAMPLES

Comparative Example 1

As shown in the process flow diagram of FIG. 3, a reaction product including isopropyl alcohol (IPA) was prepared, and a process of separating isopropyl alcohol from the reaction product was simulated using Aspen Plus available from Aspen Technology Inc.

Specifically, a feed stream was supplied at a flow rate of 10 ton/hr to a reactor operating at a pressure of 40 kg/cm²·g and a temperature of 192° C. to 208° C., a mole ratio of water (H₂O) to a propylene monomer (PP) in the feed stream was controlled to 0.4, and inert gas included ethane and propane.

The reaction product stream discharged from the reactor was supplied to the 20th stage of the absorption column 100. The total number of stages of the absorption column 100 was 20. The absorption column 100 was operated at a temperature of 96° C. to 98° C. and a pressure of 31.2 kg/cm²·g to 31.6 kg/cm²·g, isopropyl alcohol in the reaction product stream was absorbed using water supplied as a solvent in the upper end of the absorption column 100, and was separated into an upper discharge stream including a propylene monomer and a lower discharge stream including water and isopropyl alcohol. Specifically, a part of the upper discharge stream from the absorption column 100 was supplied to the gas purification column 210, the rest of the stream was refluxed to the reactor, and the lower discharge stream was supplied to the flash drum 420.

In the gas purification column 210, the upper discharge stream including the unreacted propylene monomer was refluxed to the reactor, and the lower discharge stream was supplied to the isopropyl alcohol purification section. The total number of stages of the gas purification column 210 was 32, and the operating temperature was controlled to 41° C. to 160° C. and the operating pressure was controlled to 16.50 kg/cm²·g to 16.52 kg/cm²·g.

In the flash drum 420, the upper discharge stream including the gaseous unreacted propylene monomer was refluxed to the reactor, and the lower discharge stream was supplied to the isopropyl alcohol purification section. The flash drum was operated at an operating pressure of 16.8 kg/cm²·g and the flow rate of the upper discharge stream was controlled to 0.2 ton/hr.

(1) The content of isopropyl alcohol in the upper discharge stream from the gas purification column 210 and the upper discharge stream from the flash drum 420 refluxed to the reactor, (2) the content of the propylene monomer in the upper discharge stream from the gas purification column 210 and the upper discharge stream from the flash drum 420 refluxed to the reactor, and (3) the content of the propylene monomer in the stream supplied to the isopropyl alcohol purification section are shown in Table 1.

TABLE 1

| | Example | | | | Comparative Example |
|---|---|---|---|---|---|
| | 1 | 2 | 3 | 4 | 1 |
| (1) (wt %) | 0 | 0 | 0.04 | 0 | 3.5 |
| (2) (wt %) | 94.23 | 94.23 | 94.17 | 94.17 | 83.2 |
| (3) (wt %) | 0.013 | 0.013 | 0.015 | 0.016 | 0.4 |

As shown from the results of Examples 1 to 4 in Table 1, the content of isopropyl alcohol in the stream refluxed to the reactor was as low as 0 wt % to 0.04 wt %, the content of the propylene monomer was as high as 94.17 wt % or more, and the content of the propylene monomer in the stream supplied to the isopropyl alcohol purification section was as low as 0.016 wt % or less.

In addition, in Examples 2 to 4, the inert gas in the upper discharge stream from the inert gas removal column 300 was removed and then the stream was refluxed to the reactor and reused, thereby preventing accumulation of the inert gas in the process, and thus, the production of isopropyl alcohol was increased without the use of a high-purity propylene monomer.

Separation efficiency was slightly lowered in Examples 3 and 4, in which the supply stage at which the mixed stream is supplied to the inert gas removal column 300 is out of the range according to the present invention.

In comparison, when the unreacted propylene monomer and isopropyl alcohol were separated from the reaction product stream using the absorption column 100, the flash drum 420, and the gas purification column 210 as described in Comparative Example 1, the content of isopropyl alcohol was as high as 3.5 wt % and the content of the propylene monomer was as low as 83.2 wt % in the upper discharge stream from the flash drum 420 and the upper discharge stream from the gas purification column 210 refluxed to the reactor. Thus, a reverse reaction was caused in the reactor, which reduced the production of isopropyl alcohol. In addition, the content of the propylene monomer in the stream supplied to the isopropyl alcohol purification section was as high as 0.4 wt %. Thus, an amount of the propylene monomer which was refluxed to the reactor and lost without being reused was increased.

The invention claimed is:

1. A method of preparing isopropyl alcohol, the method comprising:

reacting a propylene monomer and water in a reactor to produce a reaction product stream;

supplying the reaction product stream to an absorption column;

supplying a lower discharge stream including isopropyl alcohol from the absorption column to a gas purification column;

supplying a part of an upper discharge stream including an unreacted propylene monomer from the absorption column to an inert gas removal column;

supplying an upper discharge stream including the unreacted propylene monomer from the gas purification column to the inert gas removal column;

supplying a lower discharge stream including isopropyl alcohol from the gas purification column to an isopropyl alcohol purification section;

refluxing an upper discharge stream including the unreacted propylene monomer from the inert gas removal column to the reactor;

supplying a lower discharge stream including isopropyl alcohol from the inert gas removal column to the isopropyl alcohol purification section, supplying the lower discharge stream from the absorption column to a first flash drum;

supplying an upper discharge stream from the first flash drum to the inert gas removal column;

supplying a lower discharge stream from the first flash drum to a second flash drum;

supplying an upper discharge stream from the second flash drum to the gas purification column; and supplying a lower discharge stream from the second flash drum to the isopropyl alcohol purification section.

2. The method of preparing isopropyl alcohol of claim 1, further comprising:

passing the lower discharge stream of the absorption column through a first valve to produce a depressurized lower discharge stream from the absorption column;

supplying the depressurized lower discharge stream from the absorption column to the first flash drum;

passing the lower discharge stream of the first flash drum through a second valve to produce a depressurized lower discharge stream from the first flash drum; and supplying the depressurized lower discharge stream from the first flash drum to the second flash drum.

3. The method of preparing isopropyl alcohol of claim 1, wherein a flow rate ratio of a flow rate of the upper discharge stream from the first flash drum to a flow rate of the upper discharge stream from the second flash drum is 1:0.4 to 1:0.8.

4. The method of preparing isopropyl alcohol of claim 1, further comprising:

separating inert gas from the upper discharge stream and the lower discharge stream of the inert gas removal column.

5. The method of preparing isopropyl alcohol of claim 4, further comprising:

passing the lower discharge stream of the inert gas removal column through a third valve to produce a depressurized lower discharge stream from the inert gas removal column;

supplying the depressurized lower discharge stream from the inert gas removal column to a gas-liquid separation device;

supplying a lower discharge stream including isopropyl alcohol from the gas-liquid separation device to the isopropyl alcohol purification section; and separating an upper discharge stream including the inert gas from the gas-liquid separation device.

6. The method of preparing isopropyl alcohol of claim 1, wherein a ratio of a total number of stages of the gas purification column to a total number of stages of the inert gas removal column is 1:15 to 1:20.

7. The method of preparing isopropyl alcohol of claim 1, wherein a total number of stages of the gas purification column is 3 to 15, and wherein a total number of stages of the inert gas removal column is 50 to 90.

8. The method of preparing isopropyl alcohol of claim 1, further comprising:

forming a mixed stream of the upper discharge stream of the first flash drum, the upper discharge stream of the absorption column and the upper discharge stream of the gas purification column; and supplying the mixed stream to the inert gas removal column.

9. The method of preparing isopropyl alcohol of claim 8, wherein the mixed stream is supplied to a stage at 5% to 25% of the total number of stages of the inert gas removal column.

10. The method of preparing isopropyl alcohol of claim 8, wherein the mixed stream is supplied to a stage at 10% to 20% of the total number of stages of the inert gas removal column.

11. The method of preparing isopropyl alcohol of claim 1, wherein an operating pressure of the gas purification column is 0 kg/cm$^2$·g to 2 kg/cm$^2$·g.

12. The method of preparing isopropyl alcohol of claim 1, wherein an operating pressure of the inert gas removal column is 15 kg/cm$^2$·g to 25 kg/cm$^2$·g.

13. The method of preparing isopropyl alcohol of claim 1, wherein an operating temperature of the gas purification column is 40° C. to 80° C.

14. The method of preparing isopropyl alcohol of claim 1, wherein an operating temperature of the inert gas removal column is 40° C. to 170° C.

\* \* \* \* \*